US009680295B2

(12) United States Patent
Ryabova

(10) Patent No.: US 9,680,295 B2
(45) Date of Patent: Jun. 13, 2017

(54) ANTI-ICING COATING FOR POWER TRANSMISSION LINES

(71) Applicant: Advenira Enterprises, Inc., Sunnyvale, CA (US)

(72) Inventor: Elmira Ryabova, Sunnyvale, CA (US)

(73) Assignee: Advenira Enterprises, Inc., Sunnyvale, CA (US)

( * ) Notice: Subject to any disclaimer, the term of this patent is extended or adjusted under 35 U.S.C. 154(b) by 0 days.

(21) Appl. No.: 14/934,366

(22) Filed: Nov. 6, 2015

(65) Prior Publication Data

US 2016/0064912 A1 Mar. 3, 2016

Related U.S. Application Data

(62) Division of application No. 14/226,150, filed on Mar. 26, 2014, now Pat. No. 9,206,506.
(Continued)

(51) Int. Cl.
*H02G 7/16* (2006.01)
*B05D 7/20* (2006.01)
(Continued)

(52) U.S. Cl.
CPC ............ *H02G 7/16* (2013.01); *B05D 7/20* (2013.01); *C04B 35/453* (2013.01);
(Continued)

(58) Field of Classification Search
CPC  B05C 3/12; B05C 3/125; B05C 3/132; C23C 16/00; C23C 18/00; C23C 18/12;
(Continued)

(56) References Cited

U.S. PATENT DOCUMENTS 2,217,284 A 10/1940 Lunt
3,316,344 A  4/1967 Kid et al.
(Continued)

FOREIGN PATENT DOCUMENTS

CA    2911718       5/2016
CN  102570368 A    7/2012
(Continued)

OTHER PUBLICATIONS

EnglishTranslation of Take et al, JP 2012042354 published Mar. 1, 2012.*
(Continued)

*Primary Examiner* — Laura Edwards
(74) *Attorney, Agent, or Firm* — Kwan & Olynick LLP

(57) ABSTRACT

Provided are methods and systems for forming piezoelectric coatings on power line cables using sol-gel materials. A cable may be fed through a container with a sol-gel material having a piezoelectric material to form an uncured layer on the surface of the cable. The layer is then cured using, for example, infrared, ultraviolet, and/or other types of radiation. The cable may be suspended in a coating system such that the uncured layer does not touch any components of the system until the layer is adequately cured. Piezoelectric characteristics of the cured layer may be tested in the system to provide a control feedback. The cured layer, which may be referred to as a piezoelectric coating, causes resistive heating at the outer surface of the cable during vibration of the cable due transmission of alternating currents and environmental factors.

18 Claims, 3 Drawing Sheets

Related U.S. Application Data

(60) Provisional application No. 61/805,431, filed on Mar. 26, 2013.

(51) Int. Cl.

| | | |
|---|---|---|
| C23C 18/12 | (2006.01) |
| C23C 16/00 | (2006.01) |
| C23C 18/00 | (2006.01) |
| H01L 41/318 | (2013.01) |
| H01B 13/32 | (2006.01) |
| C23C 18/14 | (2006.01) |
| G01N 25/00 | (2006.01) |
| C04B 35/453 | (2006.01) |
| C04B 35/468 | (2006.01) |
| C04B 35/472 | (2006.01) |
| C04B 35/491 | (2006.01) |
| C04B 35/495 | (2006.01) |
| C04B 35/624 | (2006.01) |
| C04B 35/626 | (2006.01) |
| B05D 3/06 | (2006.01) |
| B05D 1/18 | (2006.01) |
| B05D 3/00 | (2006.01) |
| B05D 3/14 | (2006.01) |

(52) U.S. Cl.
CPC ........ *C04B 35/4682* (2013.01); *C04B 35/472* (2013.01); *C04B 35/491* (2013.01); *C04B 35/495* (2013.01); *C04B 35/624* (2013.01); *C04B 35/6263* (2013.01); *C04B 35/6269* (2013.01); *C23C 16/00* (2013.01); *C23C 18/00* (2013.01); *C23C 18/12* (2013.01); *C23C 18/1208* (2013.01); *C23C 18/1216* (2013.01); *C23C 18/1254* (2013.01); *C23C 18/14* (2013.01); *G01N 25/00* (2013.01); *H01B 13/322* (2013.01); *H01L 41/318* (2013.01); *B05D 1/18* (2013.01); *B05D 3/002* (2013.01); *B05D 3/067* (2013.01); *B05D 3/141* (2013.01); *B05D 2256/00* (2013.01); *C04B 2235/441* (2013.01)

(58) Field of Classification Search
CPC ............ C23C 18/1254; C23C 18/1208; C23C 18/1216; C23C 18/14; H01B 13/322; H02G 7/16; B82Y 30/00; H01L 41/318; G01N 25/00
USPC ....... 118/712, 620, 666, 670, 672, 674, 686, 118/708, 641–643, 66–68, 603, 610, 72, 118/723 R, 420, 407, 419, DIG. 11, 118/DIG. 18, DIG. 19
See application file for complete search history.

(56) References Cited

U.S. PATENT DOCUMENTS

| | | | | |
|---|---|---|---|---|
| 4,342,794 A | * | 8/1982 | Volker | ..................... B05D 7/20 118/405 |
| 5,306,560 A | * | 4/1994 | Wright | ............. C04B 35/62847 204/491 |
| 5,585,137 A | | 12/1996 | Nakamura et al. | |
| 6,037,011 A | | 3/2000 | Deegan et al. | |
| 9,206,506 B2 | | 12/2015 | Ryabova | |
| 2002/0175152 A1 | | 11/2002 | Petrenko | |
| 2010/0032081 A1 | | 2/2010 | Green | |
| 2011/0244136 A1 | * | 10/2011 | Ryabova | ................... B01F 5/10 427/428.15 |
| 2014/0295057 A1 | | 10/2014 | Ryabova | |

FOREIGN PATENT DOCUMENTS

| | | | |
|---|---|---|---|
| CN | 105283931 A | | 1/2016 |
| EP | 2979277 | | 2/2016 |
| JP | 2012042354 | * | 3/2012 |
| KR | 1020020001749 A | | 1/2002 |
| KR | 10-1647935 | | 8/2016 |
| RU | 2067345 C1 | | 9/1996 |
| RU | 2080674 C1 | | 5/1997 |
| RU | 2459329 C1 | | 8/2012 |
| RU | 2014139600 A | | 4/2016 |
| WO | 9013149 A1 | | 11/1990 |
| WO | 0052966 A1 | | 9/2000 |
| WO | 2014160773 A1 | | 10/2014 |

OTHER PUBLICATIONS

"Korean Application Serial No. 10-2015-7030580, Office Action mailed Mar. 7, 2016", 6 pgs.
"Canadian Application Serial No. 2,911,718, Office Action mailed Nov. 18, 2015", 3 pgs.
"Eurasian Application Serial No. 201500962, Office Action mailed Nov. 25, 2015", 2 pgs.
"U.S. Appl. No. 14/226,150, Non Final Office Action mailed Apr. 30, 2015", 10 pgs.
"U.S. Appl. No. 14/226,150, Restriction Requirement mailed Apr. 1, 2015", 5 pgs.
"U.S. Appl. No. 14/226,150, Notice of Allowance mailed Aug. 25, 2015", 8 pgs.
"International Application Serial No. PCT/US2014/031859, Search Report and Written Opinion mailed Aug. 21, 2014", 6 pgs.
"Int'l Application Serial No. PCT/US2014/031859, Preliminary Report on Patentability mailed Oct. 8, 2015", 5 pgs.
Rienstra, Sjoerd W. , "Nonlinear Free Vibrations of Coupled Spans of Overhead Transmission Lines", Journal of Engineering Mathematics, 53, 2005, pp. 337-348.
Scaparo, Justin et al., "Piezoelectric Energy Harvester Design and Fabrication", Proceedings of the 2012 ASEE North Central Section Conference, American Society for Engineering Education, 2012, 14 pgs.
"Chinese Application Serial No. 201480030404.3, Office Action mailed Jan. 19, 2017", 8 pgs.
"Chinese Application Serial No. 201480030404.3, Office Action mailed Aug. 2, 2016", 15 pgs.
"European Application Serial No. 14775573.0, Search Report mailed Feb. 13, 2017", 9 pgs.
"European Application Serial No. 14775573.0, Search Report mailed Nov. 7, 2016", 6 pgs.

* cited by examiner

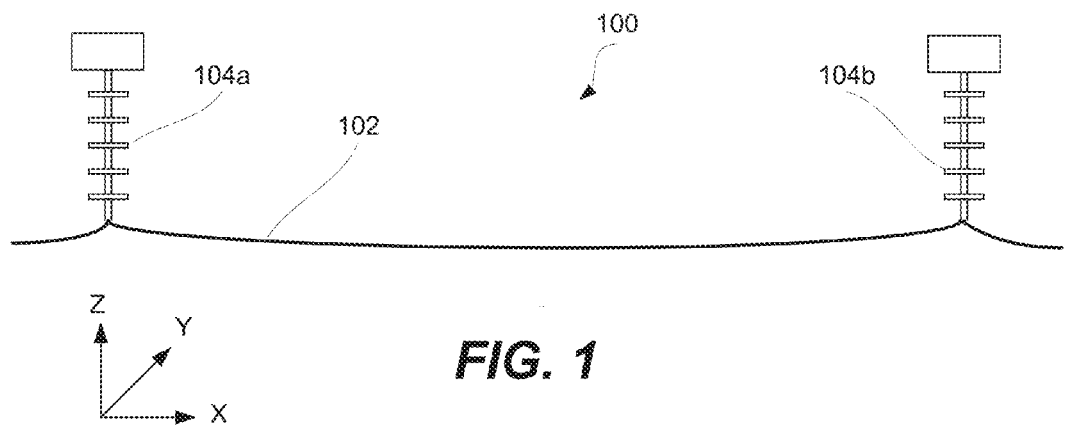
FIG. 1
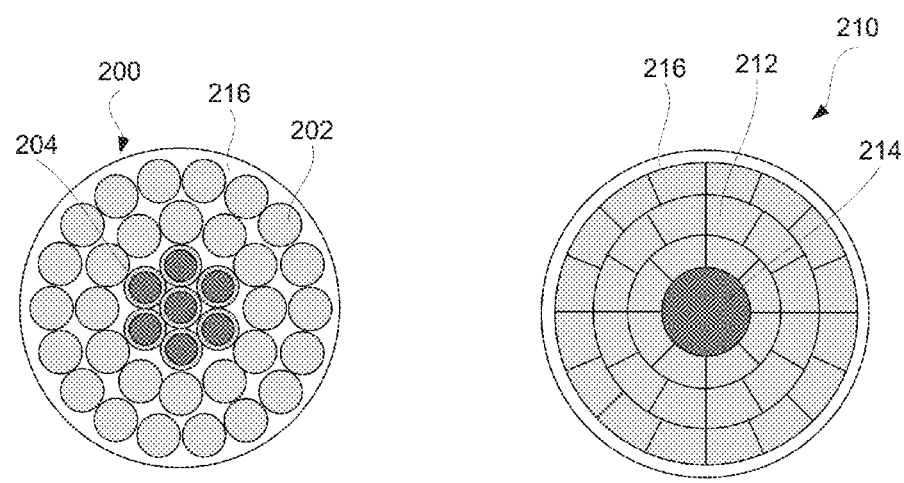
FIG. 2A   FIG. 2B
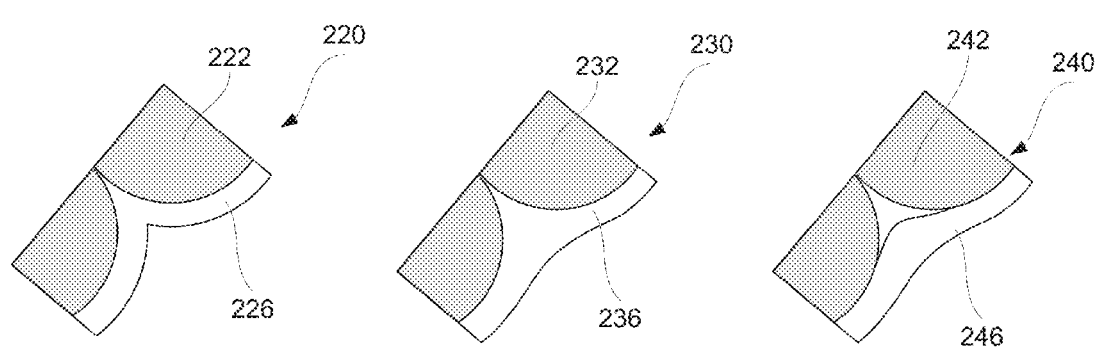
FIG. 2C   FIG. 2D   FIG. 2E

ANTI-ICING COATING FOR POWER TRANSMISSION LINES

CROSS-REFERENCE TO RELATED APPLICATIONS

This application is a divisional of U.S. patent application Ser. No. 14/226,150, entitled: "Anti-Icing Coating for Power Transmission Lines," filed on Mar. 26, 2014, now U.S. Pat. No. 9,206,506, which claims the benefit under 35 U.S.C. §119(e) of U.S. Provisional Patent Application 61/805,431, entitled: "Anti-Icing Coating for Power Transmission Lines," filed on Mar. 26, 2013, which is incorporated herein by reference in its entirety.

BACKGROUND

Icing of overhead power line cables is a major problem in many parts of the world susceptible to snow and ice storms. Ice and wet snow (collectively referred to herein as ice) can accumulate on the cables resulting in a significant additional weight and power lines becoming more susceptible to wind induced oscillation. Sufficient accumulation can even cause different cable contacting each other either directly or through the ice build-up, breaking or detaching from the supporting structures, and even collapses of the transmission towers resulting in wide spread power interruptions. The current deicing approaches are limited to physically breaking the accumulated ice off the lines. However, these approaches are time consuming and very dangerous, particularly when icy conditions complicate access to the lines by air or ground.

SUMMARY

Provided are methods and systems for forming piezoelectric coatings on power line cables using sol-gel materials. A cable may be fed through a container with a sol-gel material. During this operation, the sol-gel material is deposited as an uncured layer on the surface of the cable. This layer is then cured using, for example, infrared, ultraviolet, and/or other types of radiation. The cable may be suspended in a coating system such that the cable having the uncured layer does not touch any components of the system until the layer is adequately cured. Piezoelectric characteristics of the cured layer may be tested in the system to provide a control feedback, such as increasing the thickness of the layer. The cured layer, which may be also referred to as a piezoelectric coating, causes resistive heating at the outer surface of the cable during vibration of the cable due transmission of alternating currents (e.g., 50 Hz or 60 Hz) and environmental factors, such as winds. This localized heating may be sufficient to reducing icing on the power line cable by melting or at least softening a portion of the ice buildup at the interface with the cable.

In some embodiments, a method for forming a piezoelectric coating on a power line cable involves feeding the power line cable through a sol-gel material including a piezoelectric material. This feeding forms an uncured layer of the sol-gel material at least on an outer surface of the power line cable. In some embodiments, the entire outer surface of the power line cable is covered with the sol-gel material after this feeding operation. The method may proceed with curing the uncured layer of the sol-gel material. This curing forms the piezoelectric coating on the power line cable. The piezoelectric coating includes the piezoelectric material, which may cause resistive heating when the cable is subjected to various mechanical stresses, such as vibrations and bending.

In some embodiments, the sol-gel material is kept in a sol-gel container having a bottom. The power line cable is fed through the bottom of the sol-gel container. For example, the bottom of the sol-gel container may include a sealing port, which allows the power line cable to be fed through the bottom of the sol-gel container and prevents the sol-gel material from escaping through the bottom of the container. During the coating operation, the bottom of the sol-gel container is covered with the sol-gel material.

In some embodiments, the method also involves, prior to feeding the power line cable through the sol-gel material, exposing the power line cable to plasma. In general, the power line cable may be pretreated (e.g., using plasma) prior to forming the uncured layer of the sol-gel material on the outer surface of the power line cable, for example, to enhance adhesion between that surface and the cured layer. The pretreatment may be also used to change the surface tension during the coating operation, In some embodiments, the method also involves testing the piezoelectric coating on the power line cable for heat generation. This testing is performed after the curing operation. The testing may involve subjecting the power line cable to vibration or bending and monitoring a temperature of the piezoelectric coating while or immediately after the cable has been subjected to the vibration. For example, the cable may be bent around a roller and two or more thermocouples may be disposed prior, along, and/or after this bent to monitor the temperature of the piezoelectric coating at various stages of this test.

In some embodiments, the power line cable is a continuous cable having a length of at least about 100 meters. The power line cable may be continuously fed through the sol-gel material for an entire length of the power line cable without interruptions in the coating process or curing process. Furthermore, as noted above, the cable may be suspended in a coating system (e.g., suspended vertically) such that the cable having the uncured layer does not touch any components of the system until the layer is adequately cured. This feature helps to avoid damaging the uncured layer formed as the cable passes through and emerges from the surface of the sol-gel material in the sol-gel container.

In some embodiments, the piezoelectric coating formed on the at least outer surface of the power cable includes one of barium titanate ($BaTiO_3$), lead titanate ($PbTiO_3$), lead zirconate titanate ($Pb[Zr_xTi_{1-x}]O_3$), potassium niobate ($KNbO_3$), lithium niobate ($LiNbO_3$), lithium tantalate ($LiTaO_3$), sodium tungstate ($Na_2WO_3$), and zinc oxide ($ZnO$). Other piezoelectric materials may be used as well. In some embodiments, the sol-gel material includes polymerizable moieties.

In some embodiments, curing is performed at a temperature less than 450° C. The curing temperature may be specifically selected to prevent damage to the power line cable. For example, the power line cable may be formed at least in part from aluminum. Without being restricted to any particular theory, it is believed that aluminum starts changing its grain structure at about 450° C. resulting in a more resistive aluminum when heated above this threshold. In some embodiments, curing involves one or more of the following curing techniques: UV exposure, visible light exposure, and infrared radiation exposure. The power line cable having the uncured layer does not come in contact with any components until the uncured layer is converted into the piezoelectric coating.

In some embodiments, the piezoelectric coating is completely covers an external surface of the power line cable. Alternatively, the piezoelectric coating may be predominantly covers (e.g., greater than 50% of the external surface) but not fully covers the external surface of the power line cable. In some embodiments, the piezoelectric coating is conformal. The thickness of the uncured layer is controlled by the surface tension of the sol-gel material, the viscosity of the sol-gel material, and the feeding speed of the power line cable through the sol-gel material.

Also provided is a coating system for forming a piezoelectric coating on a power line cable. The coating system includes a coating apparatus having a sol-gel container and one or more curing units. The sol-gel container includes a bottom and a sealing port in the bottom. The sealing port is configured to allow the power line cable to be fed into the container through the bottom and to prevent a sol-gel material from escaping the sol-gel container. The coating system also includes a pre-treatment unit having a plasma delivery head. The pre-treatment unit may be disposed upstream from the coating apparatus along a feeding path of the power line cable. The one or more curing units may include one or more of the following units: an IR radiation unit, a UV radiation unit, and a microwave radiation unit.

In some embodiments, the coating system includes a testing unit for testing the performance of the piezoelectric coating. The testing unit includes a roller for controllably bending the power line cable having the piezoelectric coating and a thermal sensor for measuring a temperature of the piezoelectric coating during this bending. In some embodiments, the coating system also includes a sol-gel treatment unit for recirculating the sol-gel material from the sol-gel container and treating the sol-gel material. In some embodiments, the coating system also includes a first roller and a second roller for orienting the power line cable through the coating apparatus.

These and other embodiments are described further below with reference to the figures.

BRIEF DESCRIPTION OF THE DRAWINGS

FIG. 1 is a schematic illustration of a power line including a cable and two suspension insulated strings, in accordance with some embodiments.

FIG. 2A illustrates an example of a power line cable having multiple aluminum strands reinforced with steel strands, in accordance with some embodiments.

FIG. 2B illustrates an example of a power line cable having multiple aluminum strands reinforced with one steel strand, in accordance with some embodiments.

FIGS. 2C-2E illustrate examples of various coatings on surfaces of power line cables, in accordance with some embodiments.

DETAILED DESCRIPTION

Figure 3:
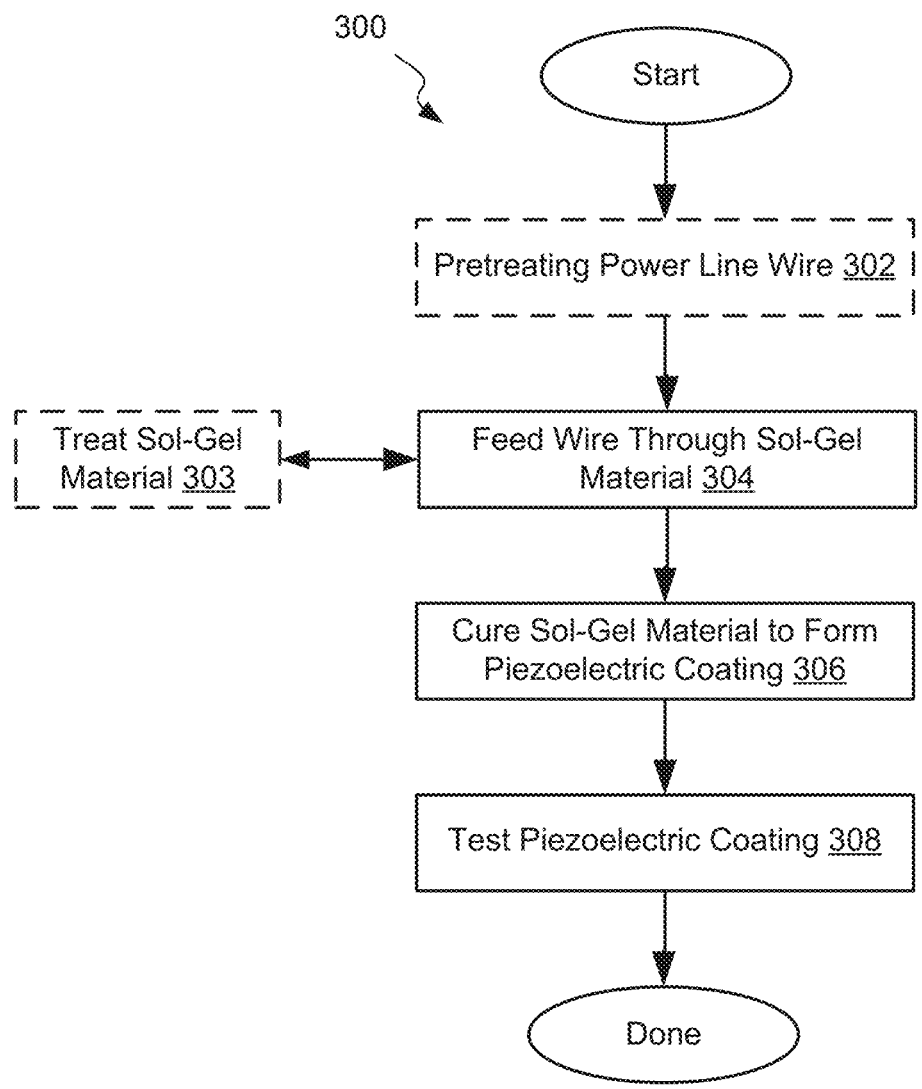
FIG. 3 is a process flow-chart of a method for forming a piezoelectric coating on a power line cable, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

Resistive heating is a viable option for deicing overhead power line cables. Some heating occurs due to electrical resistance of materials forming the cable ($P=I \times R^2$). However, this resistive heating is minimal due to the low resistance of materials used for power line cables, such as aluminum. Furthermore, this resistive heating is generated throughout the entire cable and is not localized. This distributed heat generation may not provide enough heat at the surface of the cable to break the interface with the ice buildup. The power transmission may be also down during ice storm, and the resistive heating generated during power transmission cannot be relied on in these instances.

A particular area of interest in deicing is the outer surface of a power line cable. Localized heat generating at that surface may help to melt just enough surrounding ice to break the mechanical connection between the power line cable and the ice and allow the ice to fall under the gravity. Furthermore, the outer surface of a power line cable may be modified to weaken this mechanical connection between the power line cable and the ice even before any heat is applied to the interface. For example, the surface may be modified to be smoother and/or to have a smaller contact area that allows for the ice to easily slip. Some materials may be also less sticky to ice than aluminum or, more specifically, aluminum oxide surface of a conventional power line cable. It should be also noted that the weight of the ice buildup generally helps with deicing by providing a gravitation force that pull the ice buildup away from the cable.

Power line cables described herein have piezoelectric coatings that may be used for deicing and/or other applications. These coatings may be also referred to as anti-acing coatings. A piezoelectric coating converts mechanical stresses (e.g., vibrations, bending) of the power line cable into resistive heat. Because the coating is primarily disposed on the outer surface of the conductive elements (e.g., aluminum strands), the coating causes localized heating that may be capable of melting enough ice and to break the mechanical connection between the coating and the remaining ice. Furthermore, the coating provides a smoother surface and less mechanical interface with the ice buildup. A combination of these factors help to avoid the ice buildup on the power line cables.

Piezoelectric coatings can be made from various piezoelectric materials, such as barium titanate ($BaTiO_3$), lead titanate ($PbTiO_3$), lead zirconate titanate ($Pb[Zr_xTi_{1-x}]O_3$), potassium niobate ($KNbO_3$), lithium niobate ($LiNbO_3$), lithium tantalate ($LiTaO_3$), sodium tungstate ($Na_2WO_3$), and zinc oxide ($ZnO$). These materials may be difficult, if possible at all, to deposit onto a power line cable using conventional semiconductor deposition techniques, such as chemical vapor deposition, physical vapor deposition, atomic layer deposition, and the like. First of all, power line cables are very bulky. The roll of continuous power cables may extend many meters (e.g., greater than 100 meters) in length and have to be processed without cutting the cable into shorter pieces. Furthermore, deposition has to be performed at high speeds and be relatively inexpensive. Finally, conventional semiconductor deposition techniques often require very high temperatures that exceed thresholds of power line capable materials as further described below.

Sol-gel technology provides a unique opportunity to form piezoelectric coatings on power line cables because of its specific type of precursors as well as deposition and curing techniques. Specifically, sol-gel deposition uses liquid precursors that can be handled in a high-throughput production environment. Furthermore, the liquid sol-gel materials are relatively easy to deposit onto the surface of a power line cable while the cable is being fed at high speed and cure. For example, a cable may be fed through the sol-gel material. Sol-gel materials may be solutions or colloids. A solution-type material gradually evolves towards the formation of a gel-like diphasic system containing both a liquid phase and solid phase whose morphologies range from discrete particles to continuous polymer networks. In the case of the colloid, particles are suspended in a fluid that is later removed by drying. The rate at which the solvent is removed determines porosity and microstructure of the coating. A thermal treatment, or firing process, is often used in a conventional sol-gel deposition. However, because power line cables contain materials that can drastically change their properties when exposed to high temperatures, the firing techniques is limited or not used at all. In some embodiments, a piezoelectric coating is formed from a sol-gel material without exposing the underlying power line cable to a temperature greater than 450° C.

Overall, sol-gel deposition techniques may be used for power line cable coating and precursors may be specifically formulated for low-temperature applications. The sol-gel techniques also allow for a very fine control of the coating composition and structure that ensures piezoelectric characteristics of the coating.

Power Line Cables and Vibrations

A brief description of power line cables and vibrations experience by these cables during operation may help to better understand various characteristics of piezoelectric coatings and deposition techniques described below. FIG. 1 is a schematic illustration of a power line 100 including a cable 102 and two suspension insulated strings 104a and 104b, in accordance with some embodiments. Suspension insulated strings 104a and 104b may be supported by high towers (not shown) and freely movable with respect to these support structures. In wintertime, when cable 102 is covered by snow or ice, cable 102 is vulnerable to large scale vertical vibrations in combination with a torsional vibration sustained by steady cross winds. This aero-elastic instability is known as galloping. For high enough amplitudes neighboring cables may get close enough for the air-insulation to break down, causing short-circuits and structural damage to the cables. Even a small wind force is sufficient to maintain a galloping vibration. These vibrations may involve torsional motions and horizontal cable deflections. All of these motions and vibrations may be collectively referred to as vibrations. The vibrations of a power line cable can cause mechanical stresses on the piezoelectric coating and result in a localized heating. It should be noted that the vibrations increase as ice builds up on power line cables which is when the localized heating is needed the most.

A power line cable typically uses aluminum as a conductive medium. Aluminum often forms an exterior surface of these cables. Aluminum is used because it has about half the weight of a comparable resistance copper cable even though aluminum cable have to have larger diameters due to a lower conductivity of aluminum. One type of power line cable includes multiple aluminum conductors reinforced with steel. These cables may be used for medium- and high-voltage power lines and, in some embodiments, may also be used for overhead services to individual customers.

One or more steel wires may be used to form a core of the cable and be surrounded by multiple aluminum wires. Steel wires may have aluminum shells. For example, a cable may include one steel and 6 aluminum wires, or 1 steel and 18 aluminum wires, or 1 steel and 36 aluminum wires, or 7 steel and 12 aluminum wires, or 7 steel and 26 aluminum wires, or 7 steel and 45 aluminum wires, or 7 steel and 54 aluminum wires, or 19 steel and 54 aluminum wires, or 19 steel and 84 aluminum wires.

FIG. 2A illustrates an example of a power line cable 200 having multiple aluminum strands 202 reinforced with steel strands 204, in accordance with some embodiments. Steel strands 204 may have aluminum shells. Power line cable 200 is also shown to have piezoelectric coating 216. Piezoelectric coating 216 may form a shell around external aluminum strands 202 and, in some embodiments, penetrate in between aluminum strands 202 and even steel strands 204. Piezoelectric coating 216 may be conformal as, for example, shown in FIG. 2C and FIG. 2E. Specifically, FIG. 2C illustrates an expanded view of a cable portion 220 shown two aluminum strands 222 and coating 226 conformally covering the entire surface of aluminum strands 222. In other words, coating 226 repeats the outer surface profile of aluminum strands 222. FIG. 2E illustrates another expanded view of a cable portion 240 shown two aluminum strands 242 and coating 246. A portion of the outer surface of aluminum strands 242 is not covered by coating 246 thereby creating a gap. However, the outer surface of coating 246 has a smaller surface area than the outer surface of coating 226 shown in FIG. 2C. The smaller surface area may be beneficial for reducing the contact area between the cable and ice.

In some embodiments, a piezoelectric coating may be non-conformal as, for example, shown in FIG. 2D illustrating an expanded view of a cable portion 230 having two aluminum strands 232 and coating 236. The outer surface of coating 236 has a smaller surface area than the outer surface of coating 226 shown in FIG. 2C or than the outer surface of aluminum strands 232. The smaller surface helps to reduce the contact area with ice buildups. The smaller surface also have less curvature and generally smoother, which also helps reducing the bonding strength between the cable and ice buildups. Furthermore, coating 236 may include more piezoelectric material than coating 236 shown in FIG. 2E for the same outer diameter of the power line cables. More piezoelectric material may translate in more heat generation.

Another type of power line cables uses a carbon and glass fiber core that offers a coefficient of thermal expansion about 10% of that of steel. This type of cables is referred to as aluminum conductor composite core cables and is substantially lighter and stronger than steel reinforced type. In some embodiments, composite core cables have compact trapezoidal shaped strands without any diameter or weight penalty. FIG. 2B illustrates an example of a power line cable 210 having multiple aluminum strands 212 reinforced with a steel strand 214, in accordance with some embodiments. Aluminum strands 212 have a compact trapezoidal shaped leaving substantially no space between strands 212. Furthermore, strands 212 form an even outer surface, which may be conformally covered with piezoelectric coating 216.

Processing Examples

FIG. 3 is a process flow-chart of a method 300 for forming a piezoelectric coating on a power line cable, in accordance with some embodiments. Method 300 may commence with treating the power line cable during optional operation 302. This operation may be performed prior to depositing any sol-gel material onto the cable and may be referred to as the pretreating operation. In some embodiments, operation 302 involves plasma treatment. Plasma and other types of treatment may be used to improve adhesion between the piezoelectric coating and the power line cable. In some embodiments, treatment of a power line cable may involve at least partial removal of aluminum oxide using a chemical solution.

Method 300 may then proceed with feeding the power line cable through a sol-gel material during operation 304. The sol-gel material includes components one or more piezoelectric material, such as barium titanate ($BaTiO_3$), lead titanate ($PbTiO_3$), lead zirconate titanate ($Pb[Zr_xTi_{1-x}]O_3$), potassium niobate ($KNbO_3$), lithium niobate ($LiNbO_3$), lithium tantalate ($LiTaO_3$), sodium tungstate ($Na_2WO_3$), and zinc oxide (ZnO). These components may be present in one or more sol-gel materials. For example, multiple piezoelectric materials may be used in a piezoelectric coating. These multiple piezoelectric materials may be provided in the same sol-gel material or different sol-gel materials (e.g., each sol-gel material may have a different piezoelectric material). When two or more sol-gel materials are used, a layer of one sol-gel material may be deposited and cured before depositing another layer of another sol-gel material. This feature allows controlling distribution of piezoelectric materials on the surface of a power line cable and achieving desirable piezoelectric performance. Other components sol-gel material may include one or more solvents and one or more catalysts. Various other examples and features of piezoelectric materials and sol-gel materials are described below.

During operation 304 an uncured layer of the sol-gel material is formed at least on the outer surface of the power line cable. The thickness of the uncured layer may be from about 1 nanometer to about 1 millimeter, such as between about 10 nanometers to about 100 micrometers, about 10 nanometers to about 1 micrometer, or even between about 50 nanometers to about 1 micron. The thickness may be controlled by the surface tension, viscosity, cable feeding speed and the related factors.

In some embodiments, a sol-gel material includes polymerizable moieties such as organic monomers, and cross-linkable oligomers or polymers. Examples include the base catalyzed reaction between melamine or resorcinol and formaldehyde followed by acidization and thermal treatment. In some embodiments, one or more of the metal and/or metalloid precursors includes cross-linkable monomers that are covalently attached to the metal or metalloid typically via an organic linker. Examples include di-organo-di-chloro silanes, which react with sodium or sodium-potassium alloys in organic solvents to yield a mixture of linear and cyclic organosilanes.

When cross-linkable moieties are used, the sol-gel material may also include a polymerization initiator. Examples of photo-inducible initiators include titanocenes, benzophenones/amines, thioxanthones/amines, bezoinethers, acyl phosphine oxides, benzilketals, acetophenones, and alkylphenones. Heat inducible initiators may be also be used.

During operation 304, the power line cable may be fed through the bottom of a container than holds a sol-gel material. The bottom of this container may include a sealing port. The sealing port allows the power line cable to be fed through the bottom of the container but prevents the sol-gel material from escaping through the bottom. Various features of the coating system are described below with reference to FIG. 4.

In some embodiments, method 300 involves operation 303, during which the sol-gel material provided in the container is treated. Specifically, the sol-gel material may be recirculated between this container and sol-gel treatment unit, which is further described below with reference to FIG. 4. During operation 303, the sol-gel material may be subjected to ultrasonic treatment (to break apart premature polymerization of the sol-gel material) thereby maintaining the viscosity of the sol-gel material at the desirable level. Furthermore, operation 303 may be used to maintain the temperature of the sol-gel material at the desirable level.

Method 300 may proceed with curing the uncured layer of the sol-gel material on the outer surface of the cable during operation 306. This curing forms the piezoelectric coating on the power line cable. Curing may involve exposing the uncured layer to the UV, visible, and/or infrared radiation. The radiation causes further chemical reaction of the sol-gel materials to form cured solid film. The radiation may also cause evaporation of solvents from the curing coating and increasing the temperature of the coating to form a desirable microstructure of the piezoelectric coating. The curing temperature may be less than 450° C. or even less than 400° C.

The cured piezoelectric coating applied to the power line cable is typically not annealed because some low-melting temperature materials, such as aluminum, may be used for cable construction. For example, aluminum starts changing its grain structure at about 450° C. resulting in a more resistive aluminum. Furthermore, the melting point of aluminum is about 660° C. It should be noted that conventional techniques of using sol-gel materials usually involve annealing at temperature as high as 700° C. and even 1000° C. In some embodiments, the temperature of the power line cable is kept at less than 450° C. or even less than 400° C. during the entire processing in method 300.

In some embodiments, method 300 involves testing of the cured piezoelectric coating on the power line cable for heat generation during operation 308. For example, the cable may be subjected to vibrations, bending, or other mechanical stresses and the temperature of the piezoelectric coating is monitored. In a specific embodiment, the cable is subject to a small bend as, for example, shown in FIG. 4 and further described below with reference to this figure. The temperature of the cable may be monitored at one or more locations, e.g., prior to bending, during bending, and/or after bending. The change in temperature is indicative of piezoelectric performance. The results of this testing may be used for controlling process parameters of feeding operation 304 and/or curing operation 306. For example, the feeding speed may be adjusted based on the piezoelectric performance obtained during testing operation 308.

Examples of Sol-Gel Materials

Sol-gel materials include metal or metalloid precursors and other components, such as solvents. The sol-gel materials may be in the form of a colloidal suspension of particles or a sol-gel material. The metal precursors may be organometallic compounds, metallic organic salts and metallic inorganic salts. Likewise, the metalloid precursors may be organometalloid compounds, metalloid organic salts, and metalloid inorganic salts. When multiple metal or metalloid precursors are used, one may be an organic compound, such as an alkoxide, while the other may be an organic or inorganic salt. The total amount of metal and/or metalloid precursors in the sol-gel material may be between about 5 vol % to 40 vol % or, more specifically, between about 5 vol % to about 25 vol % or even between about 5 vol % to 15 vol %.

Some examples of solvents suitable for sol-gel materials include polar protic solvents, such as organic acids or alcohols (e.g., alkyl alcohol—methanol and/or ethanol). In some embodiments, water may also be present in a sol-gel material. Polar aprotic solvents may be also used in sol-gel materials. Some examples include halogenated alkanes, alkyl ethers, alkyl esters, ketones, aldehydes, alkyl amides, alkyl amines, alkyl nitriles, and alkyl sulfoxides. More specific examples include methyl amine, ethyl amine and dimethyl formamide. For example, a metal and/or metalloid precursor may be first dissolved in a polar protic solvent, and a polar aprotic solvent is then added to the sol-gel material.

In some embodiments, the sol-gel material includes between about 50 vol % and 90 vol %, of protic solvent or, more specifically, between about 50 vol % and 80 vol % or even between about 50 vol % and 70 vol %. In the same or other embodiments, the amount of the polar aprotic solvent may be between about 1 vol % and 25 vol % of the sol-gel material or, more specifically, between about 1 vol % and 15 vol % or even between about 1 vol % and 5 vol %. The sol-gel material may also include an one or more acids or bases, which may be used as catalysts for polymerization of the metal and/or metalloid precursors.

A specific class of sol-gel materials may result in hybrid piezoelectric coatings that include inorganic and organic components. For example, organic molecules, prepolymers or polymers may be embedded in an inorganic matrix. In another example, inorganic and organic components may be connected by covalent bonds. Such hybrid piezoelectric coatings can be made by UV induced polymerization or as a product of the specific reaction.

Apparatus Examples

Figure 4:
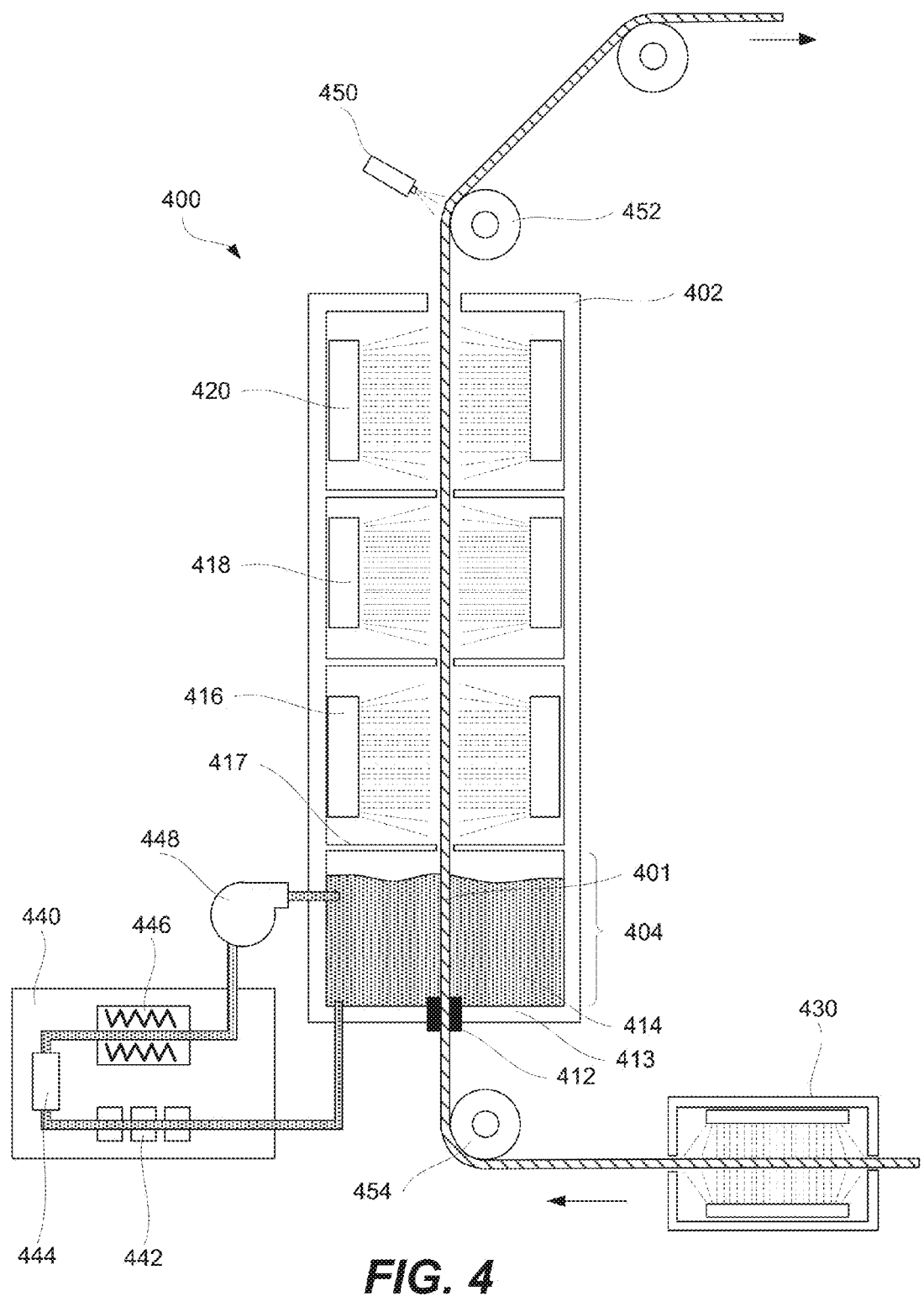
FIG. 4 is a schematic representation of a coating system for forming a piezoelectric coating on a power line cable, in accordance with some embodiments.

FIG. 4 is a schematic representation of a coating system 400 for forming a piezoelectric coating on a power line cable, in accordance with some embodiments. Coating system 400 includes at least a coating apparatus 402. In some embodiments, coating system 400 also includes one or more of the following: a pre-treatment unit 430, a sol-gel material treatment unit 440, and a testing unit 450. A fewer or more components may be included in coating system 400.

Coating apparatus 402 may include a sol-gel container 404 and one or more curing units 416-420. Sol-gel container 404 is configured to contain a sol-gel material 414 and allow for cable 401 to pass though sol-gel material 414 and form an uncured coating of sol-gel material 414 on cable 401. In some embodiments, sol-gel container 404 may include bottom 413 having a sealing port 412. Sealing port 412 allow cable 401 to pass through bottom 413 but not sol-gel material 414.

FIG. 4 illustrated three curing units 416-420, which may be configured to deliver infrared (IR) radiation, ultraviolet (UV) radiation, and/or microwave radiation. In some embodiments, apparatus 402 may include fewer or more curing units.

Curing units 416-420 may be isolated at least from sol-gel container 404 by a divider 417 to prevent curing of sol-gel material 414 within sol-gel container 404. Divider 417 allows cable 401 to pass from sol-gel container 404 and into the first of curing units 416-420 while blocking substantially all radiation from this curing unit. In some embodiments, dividers may be used between adjacent curing units 416-420, for example, to more precisely control the curing.

The piezoelectric coating on cable 401 may be substantially or completely cured when cable 401 touches a supporting roller 452. In some embodiments, cable 401 does not come in contact with any component of apparatus 402 after it comes out of sol-gel material 414. For example, cable 401 may be put to tension between rollers 452 and 454 as shown in FIG. 4.

In some embodiments, cable 401 is pre-treated between being coated with a sol-gel material. For example, cable 401 maybe passed through pre-treatment unit 430 before fed into coating apparatus 403. One examples of pre-treatment unit 430 is a plasma-pretreatment unit.

In some embodiments, sol-gel container 404 is connected to sol-gel treatment unit 440. Some coating materials, such as sol-gel materials and, in particular, non-Newtonian sol-gel materials (e.g. dilatants), commence polymerization while being held in sol-gel container 404. Sol-gel 414 may form sol-gel materials, polymerization nuclei and in some cases particulate matter. Some of these components may interfere with coating of cable 401 and should be removed from sol-gel material 414. To avoid completely discarding sol-gel material 414, sol-gel material 414 is recirculated through sol-gel treatment unit 440 that uses one or more electromagnetic transducers 442 such as ultrasonic transducers to impart ultrasonic energy onto sol-gel material 414 and to reverse the polymerization reactions. A filter 444 can optionally be employed, e.g., downstream from transducers 442 to remove any residual particulate material. In addition, a temperature control unit 446 can optionally be positioned downstream from transducers 442 to control (e.g., lower) the temperature of the fluid stream so as to prevent the onset of any additional polymerization. Sol-gel treatment unit 440 may also include pump 448 (e.g., a peristaltic pump) to circulate sol-gel material 414 through sol-gel treatment unit 440. The conduits may be made from or coated with Teflon™ or other plastic which provides a smooth interior surface in the conduit so as to minimize turbulent flow. Peristaltic pumps are also used to minimize turbulence.

Electromagnetic transducers 442 are configured convert electrical energy to pressure energy. Examples of such transducers include ultrasonic transducers that operate between about 20 KHz and about 200 MHz, more preferably between about 2 mega Hz and about 200 mega Hz. However, frequencies lower than 20 KHz can also be used. Accordingly, the range of frequency can be as low as any one of 1 Hz, 10 Hz, 100 Hz, 1 KHz, 10 KHz or 20 KHz and as high as any one of 100 KHz, 200 KHz, 500 KHz, 1 MHz, 10 MHz, 100 MHz and 200 MHz. Transducers can be obtained from any number of suppliers including Olympus Corporation in Tokyo, Japan, Omega Engineering, Inc. in Stamford, Conn., and Ultrasonic Power Corporation in Freeport, Ill.

The penetration of the transduced energy into sol-gel material 414 will depend on the choice of frequency as well as the power produced by the transducer. The choice of frequency and power will depend on the physical dimensions of the conduit, including inside diameter, conduit wall thickness and composition as well as the viscosity and velocity of sol-gel material 414 in the conduit. In order to impart energy on sol-gel material 414, in many cases two or more and as many as six or eight different frequencies may be needed to penetrate the entire volume of sol-gel material 414 passing through. The transducers can be in direct contact with the surface of the conduit or positioned within several millimeters of the conduit's surface.

In some embodiments, two or more transducers, e. g. ultrasonic transducers, are operated at a first frequency and are positioned to produce phase interference, e.g. ultrasonic phase interference in sol-gel material 414. In other embodiments, two or more additional ultrasonic transducers are used. The additional transducers operate at a different second frequency and are positioned to produce phase interference such as ultrasonic phase interference in sol-gel material 414.

Temperature control unit 446 may be used to control the temperature of sol-gel material 414, which when exposed to ultrasonic or other electromechanical energy causes the temperature of the effluent to increase. Temperature control unit 446 may reduce the temperature so that sol-gel material 414 to sol-gel container 404 is at or near the same temperature as sol-gel material 414 in sol-gel container 404.

Filter 444 may be used to remove remaining particulate matter. The filter can be positioned between transducers 442 and temperature control unit 446, between temperature control device 442 and sol-gel container 404, or at both positions.

Transducers 442 can operate at the same or different frequencies. For example, one transducer can be operated at a frequency of between 1 Hz-100 KHz or, more specifically, between 10 Hz and 100 KHz or even between 100 Hz and 100 KHz. Another transducer can operate at a different frequency such as between 1 and 500 Hz or, more specifically, between 10-500 Hz or even between 100 and 500 Hz. It should be appreciated that a multiplicity of different frequencies can be used in this embodiment, i.e., more than 2.

In some embodiments, coating system 400 may include a testing unit 450 for testing piezoelectric characteristics of the cured coating. For example, cable 401 with cured coating may be slightly bent over roller 452 thereby stressing the cured coating and the temperature of the coating is monitored with testing unit 450. Information collected by testing unit 450 may be used to control feeding speed of cable 401, radiation intensities used in curing units 416-420, and other process parameters.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A coating system for forming and testing a piezoelectric coating on a power line cable, the coating system comprising:
   a coating apparatus comprising a sol-gel container and one or more curing units,
   the sol-gel container comprising a bottom and a sealing port in the bottom,
   the sealing port configured to allow the power line cable to be fed into the sol-gel container through the sealing port and to prevent a sol-gel material from escaping the sol-gel container through the sealing port,
   the one or more curing units operable to cure the sol-gel material deposited on the power line cable leaving the sol-gel container thereby forming the piezoelectric coating on the power line cable;
   a pre-treatment unit comprising a plasma delivery head, the pre-treatment unit disposed upstream from the coating apparatus along a feeding path of the power line cable; and
   a testing unit for testing the piezoelectric coating for heat generation,
   wherein the testing unit comprises a roller for controllably bending the power line cable comprising the piezoelectric coating, and
   wherein the testing unit further comprises a thermal sensor for measuring a temperature change of the piezoelectric coating during this bending.

2. The coating system of claim 1, wherein the one or more curing units comprise a unit selected from the group consisting of an IR radiation unit, a UV radiation unit, and a microwave radiation unit.

3. The coating system of claim 1, wherein the one or more curing units comprise multiple units disposed vertically within the coating apparatus and along the feeding path of the power line cable.

4. The coating system of claim 1, wherein output the testing unit is used by the coating system for controlling feeding speed of the power line cable.

5. The coating system of claim 1, wherein output the testing unit is used by the coating system for controlling radiation intensity of the one or more curing units.

6. The coating system of claim 1, further comprising a sol-gel treatment unit for recirculating the sol-gel material from the sol-gel container and treating the sol-gel material.

7. The coating system of claim 6, wherein the sol-gel treatment unit comprises one or more electromagnetic transducers for imparting ultrasonic energy onto the sol-gel material and for reversing polymerization of the sol-gel material.

8. The coating system of claim 7, wherein the one or more electromagnetic transducers are ultrasonic transducers.

9. The coating system of claim 8, wherein different ones of the ultrasonic transducers are configured operate at different frequencies.

10. The coating system of claim 7, wherein the sol-gel treatment unit further comprises a filter for removing residual particulate materials from the sol-gel material.

11. The coating system of claim 10, wherein the filter is disposed downstream from the one or more electromagnetic transducers.

12. The coating system of claim 7, wherein the sol-gel treatment unit further comprises a temperature control unit for controlling temperature of the sol-gel material and preventing polymerization of the sol-gel material.

13. The coating system of claim 12, wherein the temperature control unit is disposed downstream from the one or more electromagnetic transducers.

14. The coating system of claim 6, wherein the sol-gel treatment unit comprises a pump for recirculating the sol-gel material through the sol-gel treatment unit.

15. The coating system of claim 14, wherein the pump is a peristaltic pump.

16. The coating system of claim 6, wherein the sol-gel treatment unit comprises a plastic conduit.

17. The coating system of claim 1, further comprising a divider isolating the sol-gel container from the one or more curing units while allowing the power line cable to pass from the sol-gel container to the one or more curing units.

18. The coating system of claim 1, further comprising a first roller and a second roller, wherein the first roller is disposed upstream from the coating apparatus along the feeding path of the power line cable, and wherein the first roller is disposed downstream from the coating apparatus along the feeding path of the power line cable, wherein the first roller and the second roller are configured to support and direct the power line cable while passing through the coating apparatus.

* * * * *